US009566150B2

(12) United States Patent
Angelopoulos et al.

(10) Patent No.: US 9,566,150 B2
(45) Date of Patent: Feb. 14, 2017

(54) EDGE DESIGN FOR REDUCING UNWANTED PHOTIC EFFECTS IN INTRAOCULAR LENSES

(71) Applicant: NOVARTIS AG, Basel (CH)

(72) Inventors: Robert D. Angelopoulos, Menlo Park, CA (US); Kamal K. Das, Arlington, TX (US); Jonathan McCann, Mansfield, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/060,144

(22) Filed: Oct. 22, 2013

(65) Prior Publication Data

US 2014/0180408 A1 Jun. 26, 2014

Related U.S. Application Data

(60) Provisional application No. 61/734,261, filed on Dec. 6, 2012.

(51) Int. Cl.
*A61F 2/16* (2006.01)

(52) U.S. Cl.
CPC ...... *A61F 2/1613* (2013.01); *A61F 2002/1696* (2015.04)

(58) Field of Classification Search
CPC .................. A61F 2002/1696; A61F 2002/169; A61F 2002/16901
USPC ........................................ 623/6.17, 6.62, 6.4
See application file for complete search history.

(56) References Cited

U.S. PATENT DOCUMENTS

| | | | | |
|---|---|---|---|---|
| 5,197,981 | A | 3/1993 | Southard | |
| 2001/0018612 | A1 | 8/2001 | Carson et al. | |
| 2003/0114926 | A1* | 6/2003 | Paul | A61F 2/1613 623/6.16 |
| 2003/0144733 | A1 | 7/2003 | Brady et al. | |
| 2005/0125055 | A1* | 6/2005 | Deacon et al. | 623/6.21 |
| 2008/0269886 | A1 | 10/2008 | Simpson et al. | |
| 2008/0269890 | A1 | 10/2008 | Simpson et al. | |
| 2009/0018651 | A1* | 1/2009 | Zhang et al. | 623/6.17 |
| 2009/0088842 | A1 | 4/2009 | Morgan | |
| 2009/0204211 | A1 | 8/2009 | Angelopoulos et al. | |
| 2011/0054603 | A1* | 3/2011 | Morgan | 623/6.43 |

FOREIGN PATENT DOCUMENTS

| | | | |
|---|---|---|---|
| CN | 101396307 | A | 4/2009 |
| CN | 101677856 | A | 3/2010 |
| EP | 1754454 | B1 | 1/2009 |
| WO | 00/66040 | A1 | 11/2000 |

* cited by examiner

*Primary Examiner* — David H. Willse
*Assistant Examiner* — Tiffany Shipmon

(57) ABSTRACT

An intraocular lens (IOL) has an optic, a peripheral rim, and a reduced thickness region connecting the optic to the peripheral rim. The peripheral rim has a continuously curving outer edge that it does not include any tangents parallel to the optical axis either along its length or at the intersection of the outer edge with the anterior or posterior surfaces of the IOL.

9 Claims, 2 Drawing Sheets

100
104
R
102
106

EDGE DESIGN FOR REDUCING UNWANTED PHOTIC EFFECTS IN INTRAOCULAR LENSES

This application claims the priority of U.S. Provisional Patent Application No. 61/734,261 filed on Dec. 6, 2012.

TECHNICAL FIELD

This invention relates generally to the field of intraocular lenses and, more particularly, to an edge design for reducing unwanted photic effects in intraocular lenses.

BACKGROUND OF THE INVENTION

The human eye in its simplest terms functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL). In the United States, the majority of cataractous lenses are removed by a surgical technique called phacoemulsification. During this procedure, an opening is made in the anterior capsule and a thin phacoemulsification cutting tip is inserted into the diseased lens and ultrasonically vibrated. The vibrating cutting tip liquefies or emulsifies the lens so that the lens may be aspirated out of the eye. The diseased lens, once removed, is replaced by an IOL.

A known difficulty for intraocular lenses has been that off-axis light rays can be reflected or transmitted into the visual field, producing undesirable photic effects. Edge designs for IOLs have been proposed to steer the unwanted light rays to different locations, but depending on the incident angle of the incoming light, this may not address the problem sufficiently and may inadvertently create new photic effects. The problems may be exacerbated in thin lens designs that use particular edge shapes for mechanical stability. There accordingly remains a need to reduce these undesired photic effects.

DETAILED DESCRIPTION

Various embodiments of the present invention provide shaped edges for IOLs to reduce photic effects. In particular embodiments, an anterior surface of the IOL is formed with a continuously curving edge that redirects transmitted and reflected off-axis light to reduce negative visual effects. In certain embodiments, a continuously curving edge may also be employed in conjunction with a thickened periphery to allow for improved mechanical stability in relatively thin lenses. Further feature and advantages of various embodiments will be apparent from the following detailed description.

Foldable IOL designs using a thickened rim for improved mechanical stability are disclosed, for example, in United States Patent Application Publication No. 2009/0088842, which is incorporated herein by reference. Such designs may include a recessed surface on the anterior and/or posterior face of the lens around an edge of the optic, thereby reducing the overall bulk of the optic. The recessed surface is in turn surrounded by the thickened rim attached to the haptics, providing additional mechanical stability to prevent the optic from buckling or tilting. The interaction between the rim and incoming off-axis light rays can produce unwanted photic effects that can deteriorate visual quality for the IOL patient. Various embodiments of the present invention provide an improved edge design for such IOLs that reduces these unwanted photic effects.

Figure 1:
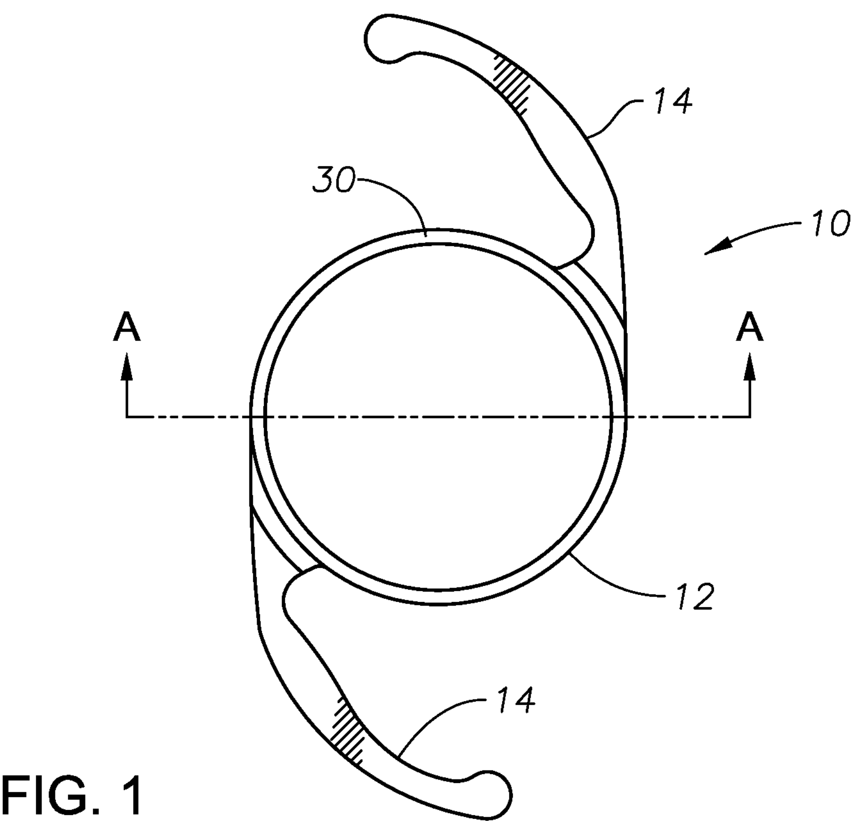
FIG. 1 illustrates an example IOL according to a particular embodiment of the present invention.

FIG. 1 illustrates an example IOL 10 according to a particular embodiment of the present invention. IOL 10 is formed from as a single-piece from a soft, foldable, biocompatible material of any of the numerous such materials known by those skilled in the art, including by not limited to silicone, hydrogel and soft acrylic materials that may also include compounds to absorb specific wavelength ranges of light (such as ultraviolet light). In the depicted embodiment, IOL 10 includes optic 12 and haptics 14. Optic 12 refers to the central region of the IOL 10 that is configured to focus incoming light onto the retina to provide vision to the patient. The optical axis of the optic 12 corresponds to the direction of parallel light rays from a distant object that are focused by the optic 12. The optical surface of the optic is defined as the region having a base curvature determining the optical power of the optic, with the outer boundary of this optical zone defining an edge thickness of the optic ("thickness" in this context referring to a thickness along the optical axis). The diameter of the optical surface is preferably in the range of 4.5-7.0 mm, corresponding to an ordinary range of pupil diameters in patients.

In the depicted embodiment, optic 12 is depicted as a monofocal refractive optic with a radius of curvature determining the optical power of the optic 12. In principle, however, optic 12 could have any suitable structure for focusing light onto the retina, which may include diffractive or refractive elements. Optic 12 may also include suitable modifications for correcting monochromatic or chromatic aberrations (including but not limited to spherical aberrations of any order, coma, astigmatism), including such means as toric or aspheric optical surfaces. Hence, it should be apparent to one skilled in the art that any number of known optical designs for IOLs can be included in various embodiments of the present invention.

IOL 10 is depicted as an IOL typically implanted in the capsular bag, but various embodiments of the present invention could include phakic IOLs placed in the anterior chamber of the eye or sulcus-fixated lenses for the posterior chamber. Haptics 14 can include any mechanical support structure for the IOL that maintains the IOL in place in the appropriate anatomical location. The haptics 14 shown in the depicted embodiment are typical for placement in the capsular bag, but one skilled in the art will be aware of numerous other modifications to the depicted structure. The haptics 14 are shown as being formed integrally with the rest of the IOL 10, but they could also be separate pieces attached to the periphery of the IOL 10.

Rim 30 is a thickened outermost periphery of the IOL 10 integrally formed with optic 12 that is joined to the haptics 14 and that provides mechanical stability for the optic 12 when the IOL 10 is in place. The rim 30 is connected to a reduced thickness region relative to the edge of the optical surface (where thickness is measured along the optical axis of the IOL 10) that surrounds the optical surface. The rim 30 is thickened relative to this reduced thickness region. In order to provide an advantageously thin IOL profile, the rim should have a thickness of 0.3 mm or less relative to an expected optic thickness of 0.19 mm-0.45 mm with the reduced thickness region being 0.1 mm thick or less. However, depending on the optical power requirements of the lens, much thicker lenses may be required, so that the rim 30 and the reduced thickness region of the optic 12 could be thicker while still allowing the optic 12 to remain stable with a relatively smaller thickness than if the rim 30 were not present.

Figure 2:
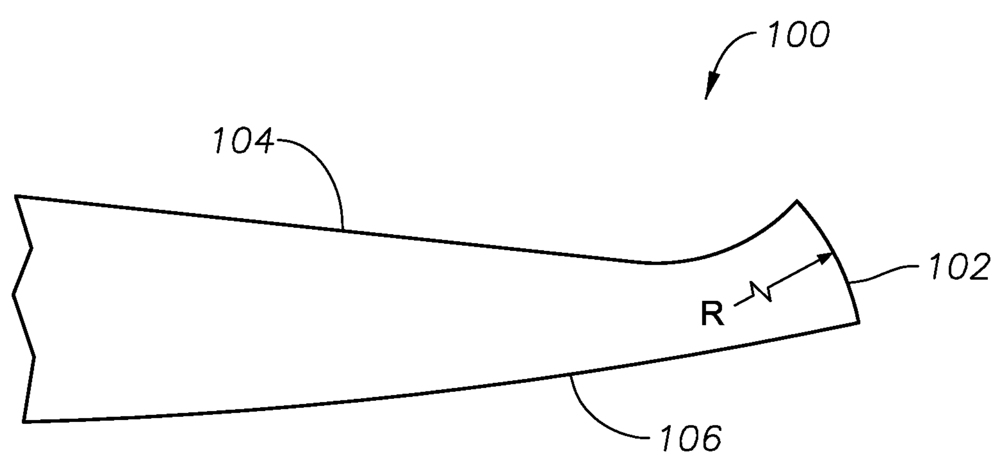
FIG. 2 illustrates a cross-sectional view of a particular embodiment of an IOL with a continuously curving outer edge.

FIG. 2 shows a cross-sectional view of a particular embodiment of an IOL 100 with a continuously curving outer edge, with the cross section taken along line A-A of FIG. 1. The outer edge 102 faces outwardly from the optical axis, and it extends between the anterior surface 104 and the posterior surface 106 of the IOL, meeting the respective surfaces 104 and 106 at corners, which may be sharp discontinuities or somewhat more gradual reversals of the profile of the surface long the optical axis. The outer edge 102 is “continuously curving,” which is to say that it does not include any tangents parallel to the optical axis either along its length or at the intersection of the outer edge 102 with either of the surfaces 104 and 106. In particular embodiments, the radius of curvature of the continuously curving outer edge 102 may be constant and relatively gradual, such as 0.8 mm. In other embodiments, the radius of curvature of the continuously curving outer edge may be relatively steep, such as 1.19 mm. By presenting a relatively large surface area to incoming light without any consistent surface orientation, the continuously curving edge thereby prevents any substantial transmission of off-axis light through the edge to any particular location as well as distributing internally reflected light away from the fovea of the retina. The combination of these features thus reduced undesired photic phenomena.

Advantageously, the continuously curving edge may also be configured to direct light to particular locations. For example, a first portion of the outer edge 102 may have a configuration (orientation and curvature) to reflect internal light rays to a location within the body of the optic 12, while a second portion of the outer edge 102 may have a curvature such that it reflects incoming light rays outside of, and generally posterior to, the body of the optic 12. This combination helps to redirect off-axis light away from the visual field. Additionally, the outer edge 102 and/or the periphery of the anterior and/or posterior surfaces 104 and 106 may be textured, coated, or the like to diffuse or absorb incoming light to some degree, which can further reduce unwanted photic effects.

Figure 3:
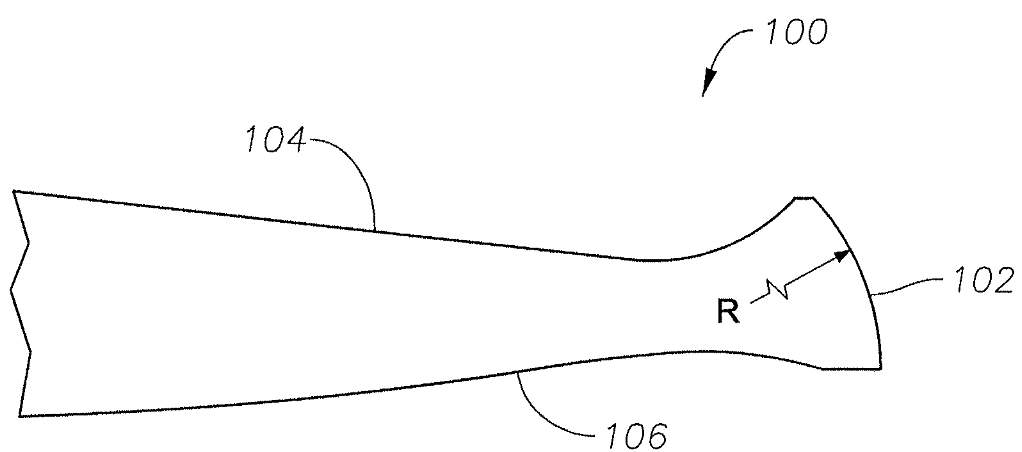
FIG. 3 illustrates a cross-sectional view of another particular embodiment of an IOL with a continuously curving edge having recessed surfaces.

In the depicted embodiment of FIG. 2, the reduced thickness region around the optic 12 is formed by a recess in the anterior surface 104 outside of the optical surface of the optic 12, while the posterior surface 106 has a continuous curvature until the corner at which the posterior surface 106 intersects the outer edge 102. In combination with the features of the outer edge 102, this facilitates the ability of the outer edge 102 to redirect light away from the visual field. FIG. 3 shows an alternative embodiment in which both the anterior surface 108 and the posterior surface 110 are both recessed to form the reduced thickness region. Relative to a flat outer edge, the continuously curving outer edge 102 will still produce reduced photic effects, but the recessed posterior surface 110 may tend to direct light rays closer to the fovea, which can make photic effects more significant relative to the embodiment shown in FIG. 2. However, the continuously curving edge design can still provide improved performance under these circumstances.

Figure 4:
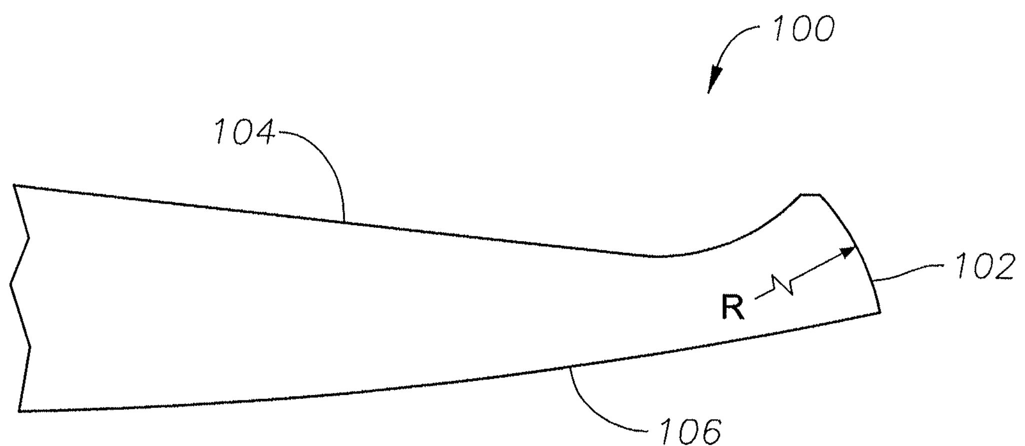
FIG. 4 illustrates a cross-sectional view of another particular embodiment of an IOL that includes a flat, anterior-facing surface meeting the reduced thickness region.

In the depicted embodiment of FIG. 2, the anterior surface 104 of the IOL meets the peripheral rim 102 at a sharp discontinuity. FIG. 4 illustrates an alternative embodiment in which the anterior surface 104 of the peripheral rim 102, having the same maximum thickness, includes a flat, anterior-facing surface meeting the reduced thickness region. As in the case of FIG. 3, there may be additional photic effects associated with the flat portion of the anterior surface, such as transmission of off-axis light rays, but these effects will nonetheless be mitigated to some extent by the continuously curving outer edge.

Those having ordinary skill in the art will appreciate that various changes can be made to the above embodiments without departing from the scope of the invention.

What is claimed is:

1. An intraocular lens (IOL) formed from a soft, foldable material, comprising:

an optic having an optical surface with a base curvature corresponding to an optical power of the optic, the optic having an edge thickness at an outer boundary of the optical surface;

a peripheral rim formed as a circle surrounding the optic, the peripheral rim having a maximum thickness, the peripheral rim defining a cross section having a continuously curving outer edge having a constant radius and that does not include any tangents parallel to an optical axis of the optic, the continuously curving outer edge extending between the anterior and posterior surfaces of the IOL and intersecting each surface at a respective corner; and a reduced thickness region outside the optical surface of the optic between the peripheral rim and the optic, the reduced thickness region integrally formed with the peripheral rim and the optic and having a reduced thickness relative to the maximum thickness of the peripheral rim and the edge thickness of the optic.

2. The IOL of claim 1, wherein the continuously curving outer edge comprises a first portion having a curvature configured to reflect off-axis light rays within the optic and a second portion having a curvature configured to reflect off-axis light rays posterior to the optic.

3. The IOL of claim 1, wherein an anterior surface of the IOL is recessed to form the reduced thickness region.

4. The IOL of claim 3, wherein both the anterior surface of the IOL and a posterior surface of the IOL are recessed to form the reduced thickness region.

5. The IOL of claim 1, wherein the optic is a monofocal refractive optic.

6. The IOL of claim 5, wherein the optic is toric, aspheric or both.

7. The IOL of claim 1, wherein at least out of the outer edge, an anterior surface of the IOL, and a posterior surface of the IOL is textured to diffuse incoming light.

8. The IOL of claim 1, wherein a radius of curvature of the outer edge is 0.8 mm.

9. The IOL of claim 1, wherein a radius of curvature of the outer edge is 1.19 mm.

* * * * *